United States Patent [19]

MacMillan et al.

[11] Patent Number: 4,951,655
[45] Date of Patent: Aug. 28, 1990

[54] MAXILLARY FIXED CERVICAL SPINE ORTHOSIS

[75] Inventors: Michael MacMillan; Christopher Schirmer, both of Gainesville, Fla.

[73] Assignee: University of Florida, Gainesville, Fla.; by said Michael MacMillan

[21] Appl. No.: 329,278

[22] Filed: Mar. 27, 1989

[51] Int. Cl.⁵ ............................................. A61F 5/08
[52] U.S. Cl. ................................... 128/76 R; 128/78; 128/846; 128/861; 128/869
[58] Field of Search ............... 128/857, 859, 860, 861, 128/75, 76 R, 87 R, 84 R, 87 A, 89 A, 97.1, 78, 85; 433/5

[56] References Cited

U.S. PATENT DOCUMENTS

| | | | |
|---|---|---|---|
| 2,102,069 | 9/1936 | Hanicke | 128/DIG. 23 |
| 2,166,229 | 7/1939 | Anderson | 128/84 R |
| 2,492,383 | 12/1969 | Jones | 128/857 |
| 2,550,869 | 5/1951 | Salisbury | 128/89 A |
| 2,565,123 | 8/1951 | De Mar | 128/97.1 |
| 2,681,058 | 6/1954 | Mathues | 128/89 A |
| 2,705,006 | 3/1955 | Cettel et al. | 128/857 |
| 3,527,219 | 9/1970 | Greenberg | 128/861 |
| 3,596,655 | 8/1971 | Corcoran | 128/75 |
| 4,194,501 | 3/1980 | Watt | 128/75 |
| 4,383,523 | 5/1983 | Schurman | 128/78 |
| 4,620,530 | 11/1986 | Lanier et al. | 128/75 |

Primary Examiner—Robert A. Hafer
Assistant Examiner—Charles H. Sam
Attorney, Agent, or Firm—Kerkam, Stowell, Kondracki & Clarke

[57] ABSTRACT

A cervical spine orthosis is provided which comprises an upper body engaging member, such as a vest, a front and rear pair of rigid vest uprights, and a band encircling the head of the wearer at the level of the wearer's mouth, the bank being securely fastened to the vest uprights, and carrying a maxillary bridge comprising a maxillary tooth splint adapted to engage the upper set of teeth of the wearer and a bridge member attached to and spanning the distance between the band and the maxiallary tooth splint. The band further has attached thereto, two occipital support pads which are adapted to engage the neck of the wearer at the occipital bone region at the posterior base of the skull, the support pads being movable into an engaging position with the neck by use of threaded positioning screws. Improved immobilization and/or control of movement the cervical spine are provided.

19 Claims, 4 Drawing Sheets

MAXILLARY FIXED CERVICAL SPINE ORTHOSIS

BACKGROUND OF THE INVENTION

1. Field of the Invention

The present invention relates to cervical orthoses, and more specifically to an orthosis for stabilizing the cervical spine employing maxillary and occipital fixation.

2. Description of Related Art

Heretofore, numerous orthotic devices have been developed whose purpose is to control, restrict, or stabilize cervical motion, or to fully immobilize the cervical spine. The known devices may be generally characterized as falling into one of two groups, a first group providing fully adequate, nearly complete immobilization or securing of the cervical spine, at the sacrifice of patient comfort, and a second group of devices providing relief from patient discomfort while sacrificing the adequate immobilizing or securing properties of the device.

Several types of available cervical orthoses are described in Sypert, G. W.; "External Spinal Orthosis", Neurosurgery; April 1987, 20(4): p. 642–9. The basic cervical collar discussed therein has a major disadvantage in that the collar does little to restrict cervical motion or to transfer weight off of the cervical spine. The "poster-type" orthosis, known by such names as the "Guilford orthosis" or the "S.O.M.I." (Sternwoocipital Mandibular Immobilized), has a major disadvantage in that this type of brace poorly controls upper cervical flexion, as well as rotational and lateral bending motion of the cervical spine. A further type of orthosis, termed a "cervicothoracic orthosis", described in Sypert allows up to 50% unrestricted lateral bending as well as permitting some amount of flexion and extension of the cervical spine.

The "halo" orthosis, described in Sybert as well as in other publications and patents, is currently believed to be the most secure means of controlling cervical motion in flexion, extension, lateral bending, and rotation. The halo orthosis device derives its name from the use in the orthosis of a halo or ring which is rigidly attached, by pins or bolts, into the skull of the patient. The ring or halo is held rigidly in place by a support mechanism comprising a vest or harness attached to the patient's upper body and a plurality of rigid upright posts connected to and extending between the vest and the halo.

Use of the halo orthosis carries very significant risks due to various complications which may arise from use. Potential complications, in addition to severe patient discomfort, include pin track infection, unsightly scarring, brain abcess, penetration of the skull, and subdural empyema.

Various braces and orthoses are also disclosed in U.S. Pat. Nos. 4,735,196; 4,383,523; 4,643,174; 4,477,041; and 3,724,452. Each of these devices shares one or more of the above-mentioned disadvantages. For example, U.S. Pat. No. 4,735,196 discloses a halo-type orthosis designed to increase patient comfort and increase stabilization of the cervical spine by altering the upper body support design from those known in the art. This device still requires the use of pins partially embedded in the skull as the head stabilizing attachment. Heretofore lacking in the cervical spine braces or orthoses previously known in the art is an orthosis which provides full or nearly full immobilization capabilities while eliminating the potential complications, risks and discomfort associated with the halo-type orthosis.

It is therefore an important object of the present invention to provide a cervical spine orthosis having substantially all of the positive attributes of halo-type orthosis, while substantially eliminating the negative attributes of such an orthosis.

It is a further object of the present invention to provide a cervical spine orthosis having a vest or upper body support member, a plurality of rigid uprights, and a maxillary bridge and occipital support pads attached to a metal band, the uprights being attached between the upper body support member and the metal band.

It is a further object of the present invention to provide a maxillary bridge component adapted to be attached to a surrounding band and rear support means also attached to the band, the bridge component and rear support means being readily adapted to be used in place of a skull-penetrating halo in a halo-type orthotic device.

SUMMARY OF THE INVENTION

The above and other objects of the present invention are accomplished by providing a cervical spine orthosis having means adapted to securely engage the superior maxillary teeth of the wearer and the occipital bone of the wearer, and to securely engage the upper body of the wearer, and having rigid connecting means connected to and extending between the superior maxillary teeth and occipital bone engaging means and the upper body engaging means.

In a first embodiment, the present invention provides a cervical spine orthosis comprising an upper body engaging means for securely engaging an upper body of a wearer, a maxillary tooth splint means for securely engaging a plurality of superior maxillary teeth of the wearer, support means for engaging a back of a head of wearer, the wearer at a region where the occipital bone is located, and means for rigidly connecting the maxillary tooth splint means and the occipital support means to the upper body engaging means wherein relative movement between the maxillary tooth splint means, the occipital support means, and the upper body engaging means is substantially prohibited.

In a further embodiment, the invention comprises a component for a cervical spine orthosis which comprises a maxillary tooth splint means for tightly and securingly engaging a plurality of superior maxillary teeth of a wearer, rear support means for engaging a back portion of a head of the wearer, and means for rigidly connecting the splint means and the rear support means to a support member disposed on an upper body of the wearer, wherein relative movement between the splint means, the rear support means, and the upper body support member is substantially prohibited.

In a further variation of the present invention, a method for stabilizing a cervical spine of a patient is provided, which comprises the steps of:

(a) attaching an upper body engaging means to an upper body of the patient;

(b) securing a maxillary tooth splint means to the upper maxillary teeth of the patient;

(c) attaching the maxillary tooth splint means to a band which is adapted to encircle the head of the wearer;

(d) positioning a pair of support pads to brace an occipital bone of the wearer, the support pads being secured to the band at a rear portion thereof; and (e) connecting, in a rigid manner substantially prohibiting relative movement, the upper body engaging means and the band having the maxillary tooth splint means and the support pads attached thereto.

BRIEF DESCRIPTION OF THE DRAWINGS

These and other features of the present invention and the attendant advantages will be readily apparent to those having ordinary skill in the art, and the invention will be more easily understood from the following detailed description of the preferred embodiments of the present invention taken in conjunction with the accompanying drawings, wherein like reference characters represent like parts throughout the several views and wherein.

DETAILED DESCRIPTION OF THE PREFERRED EMBODIMENT

Figure 1:
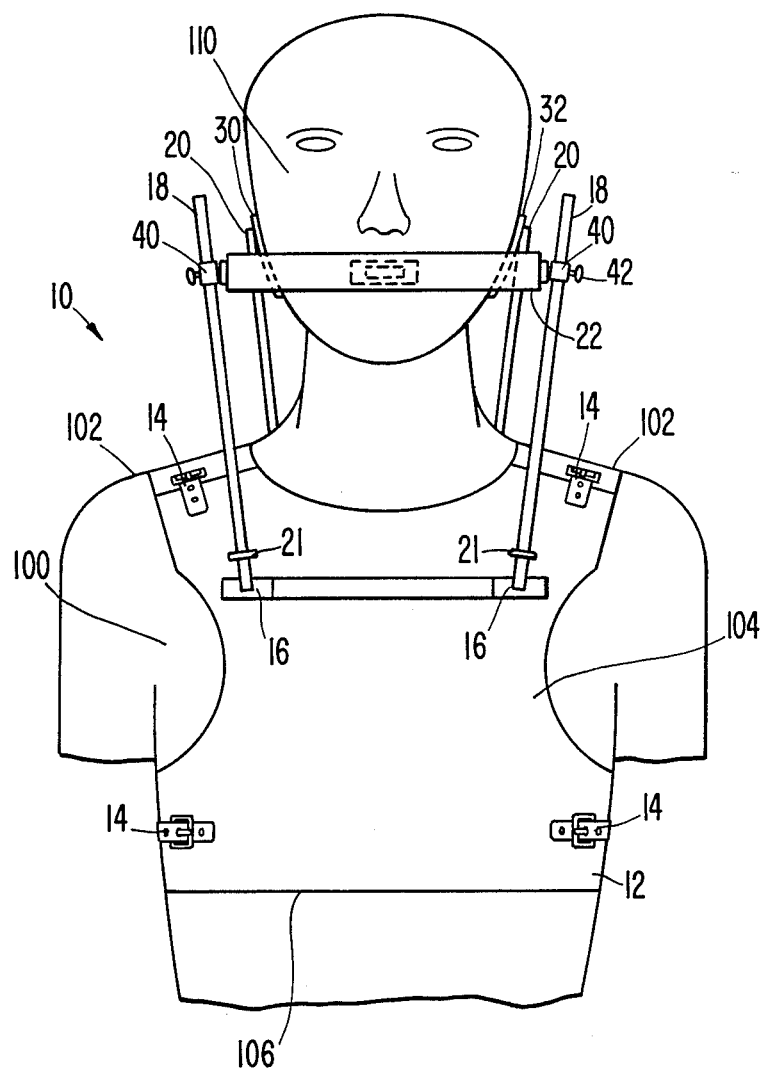
FIG. 1 is a front elevation view of a cervical spine orthosis according to a preferred embodiment of the present invention.

Referring initially to FIG. 1, a cervical spine orthosis according to a preferred embodiment of the present invention is designated as numeral 10. The orthosis comprises an upper body member depicted as vest 12, which may be made of a rigid or semi-rigid material. The vest 12 securely engages the upper body 100 by encircling the trunk over a large area, including, for example, the upper aspect of the shoulders 102, the chest or pectoralis major muscle 104, and the upper abdomen 106. The vest 12 may be provided with adjustment strap-and-associated buckle assemblies 14, in order to tighten the engagement of the vest to the upper body.

The depicted vest 12 roughly resembles the commonly known and previously used halo-type vest, used in conjunction with the aforementioned skull-engaging halo structure. One example of this type of vest is manufactured by Ace Medical, of Los Angeles, Calif. The specific details as to how the vest or upper body engaging member 12 is fitted to the body 100 may be varied from the depicted embodiment and those specific details do not form a part of the present invention.

Vest 12 is provided with at least two attachment points 16 at the front and at the rear of the vest, where front vest uprights 18 and rear vest uprights 20 are mounted to the vest. The uprights 18, 20, will also preferably be of the type used on known halo-type orthoses. The uprights are preferably cylindrical steel rods, each of which is provided with one or more angle or size adjusting means 21 which may be locked into a fixed position once a proper orientation for the upright has been established.

A band or halo 22 is provided in the depicted preferred embodiment which is adapted to encircle the head of the wearer at approximately the level of the wearer's mouth. As can be seen in greater detail in FIGS. 3, 4 and 5, the band is provided with maxillary splint means 24 at a front portion of the band, the maxillary splint means in the embodiment depicted in FIGS. 3 and 4 comprising a maxillary splint 26, and a bridging member 28 extending from splint 26 and adapted to connect to an inner surface of band 22, by any of a variety of connector types, an example being machine screws threaded into tapped bores in the bridging member 28 and band 22.

Figure 3:
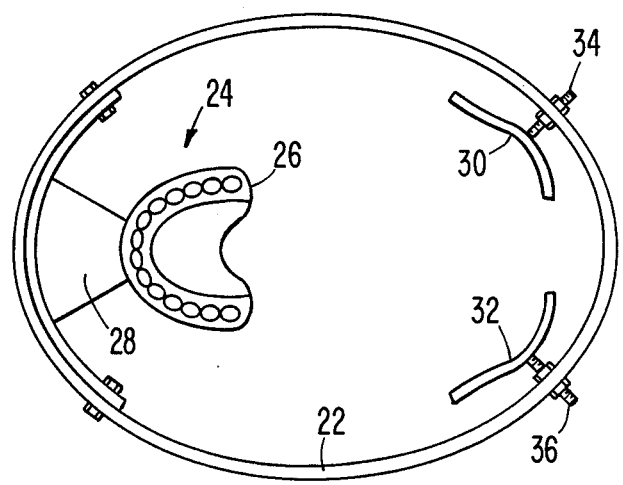
FIG. 3 is a top plan view of the band portion of the cervical spine orthosis of the present invention having the maxillary bridge and occipital support pads attached thereto.
Figure 4:
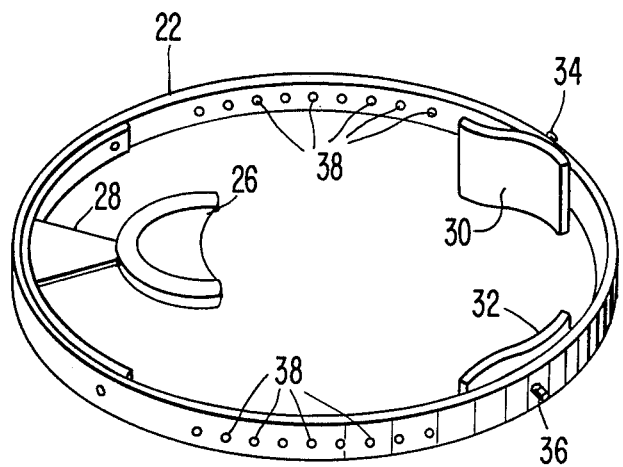
FIG. 4 is a perspective view of the band portion having the maxillary bridge and occipital support pads attached thereto.

The maxillary splint 26 depicted in FIGS. 3 and 4 may advantageously be formed for each individual patient or wearer, as this splint 26 comprises a mouthpiece shaped to engage at least a plurality of the teeth in the upper set of teeth extending from the superior maxillary bone in the skull, or maxillary teeth, as termed herein. The splint or mouthpiece 26 may be formed by taking stone impressions of the superior maxillary teeth, and using the impressions as a mold to form and shape an acrylic material to produce the appropriate tooth-receiving areas in the splint. The maxillary splint 26 is preferably attached to bridging member 28 by an acrylic cement or compound.

At a rear portion of band 22, on opposite sides of a central portion thereof, are disposed a pair of occipital support pads 30, 32, contoured to substantially conform to the shape of the back 108 (FIG. 2) of the wearer's head and neck, and to engage the base or posterolateral aspect of the skull at the occipital bone. The occipital support pads 30, 32, are mounted on band 22 by way of threaded positioning screws 34, 36, extending from a rear side of the pads through band 22. As will be discussed in more detail later, the positioning screws permit adjustment of the position of the pads as required to properly engage the area at the rear base of the skull.

The band may be designed to be adjustable in size, although adjustment means are not specifically depicted in the figures. Such adjustment means may be provided in the form of an overlapping segment of the band which would allow expansion or contraction of the band as necessary, and such an adjustable band would have means for locking the band once a proper size has been attained.

A series of bores 38 (FIG. 4) are depicted on either side of the band, the bores being adapted to receive fastners extending from band-positioning lugs 40, best seen in FIG. 1, the lugs 40 securely connecting the band 22 to the vest uprights 18. These lugs 40 advantageously have bores extending therethrough which allow relative sliding movement of the lugs along the uprights. The lugs also preferably have means for locking the position of the lugs 40 on the vest upright 18, depicted in FIG. 1 as thumbscrews 42, although set screws or other appropriate locking means may be employed. The slideable, locking lugs permit a limited amount of height adjustment in properly positioning the band to fix the wearer's head in the proper orientation.

The sequence for assembly of the orthosis 10 and the installation of the orthosis on the patient/wearer begins with securing the maxillary splint 26 of the maxillary bridge to the superior maxilla of the patient. This may advantageously be accomplished by the addition of an acrylic adhesive compound, or alternatively by wiring the splint to the superior maxilla or superior maxillary teeth. Once the maxillary bridge 24 is secured, the band or halo 22 is fastened to the bridge by, for example, machine screws. The occipital support pads are then adjusted, by way of positioning screws, in a posterolateral aspect of the occiput, so as to conform to and remain in contact with the posterior aspect of the head in the region of the base of the skull. The direction of movement of the occipital support pads may be characterized as a substantially radial movement with respect to band 22, and when the pads are moved, the space between the pads and the perimeter of the band 22 is changed.

Figure 2:
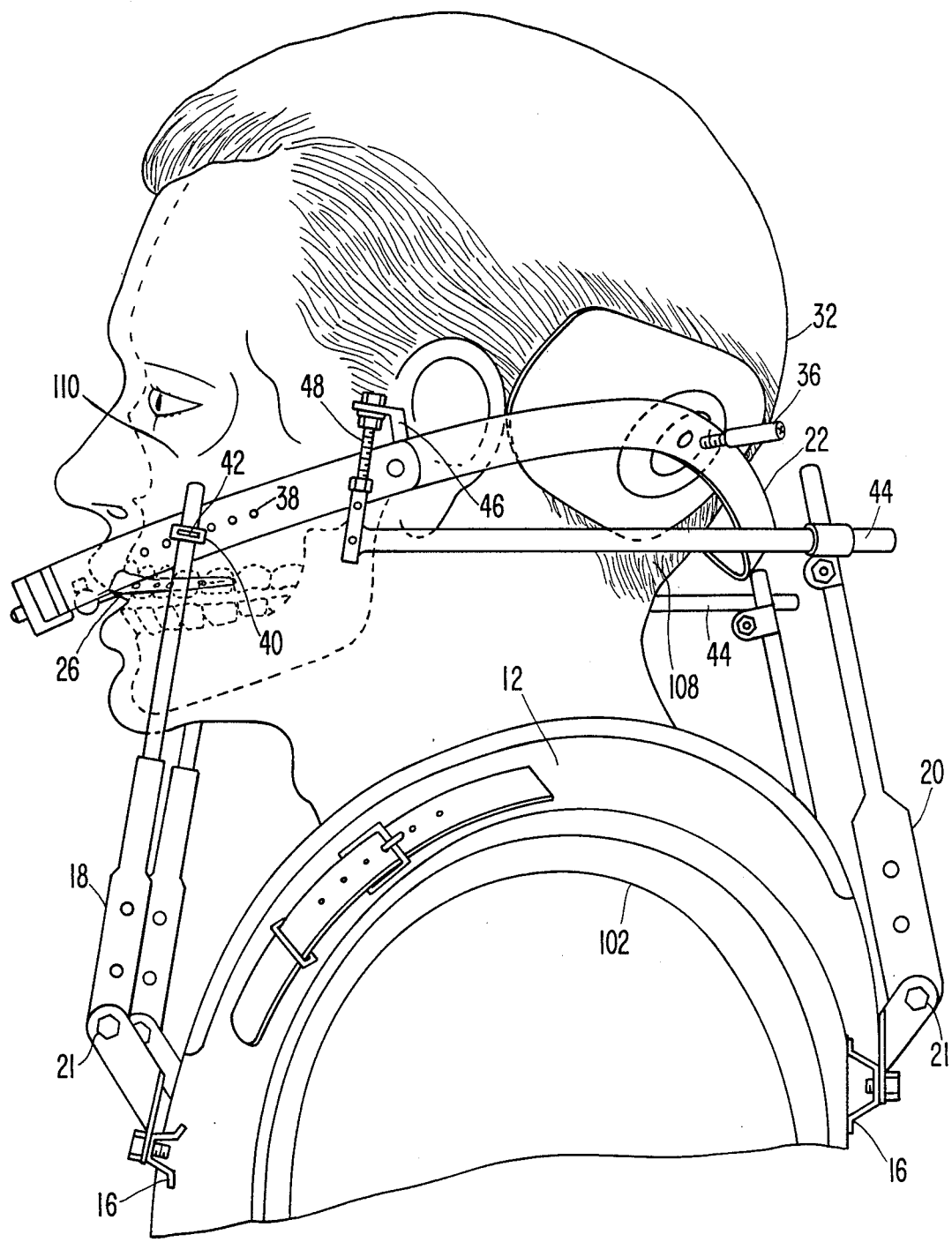
FIG. 2 is a side elevation view of the cervical spine orthosis.

The vest or upper body support 12, with uprights 18, 20 is installed on the patients' body in a separate step, which may be performed before or after the above-described installation of the band assembly. Once the vest and band have been installed on the respective body parts, the band 22 may then be attached to the vest uprights 18 by attaching lugs 40 to band 22, in a position wherein the cervical spine is in the desired position. As seen in FIGS. 1 and 2 the pair of front vest uprights 18 20 are preferably attached to the band at the front of the band, and just to the side of face 110 of the wearer. The pair of back vest uprights 20, as depicted in FIG. 2, preferably have horizontal extension members 44 which extend forward to approximately just forward of the ear 112, and attach to band side flanges 46 (FIG. 5) by way of an adjustable height threaded post 48.

Figure 5:
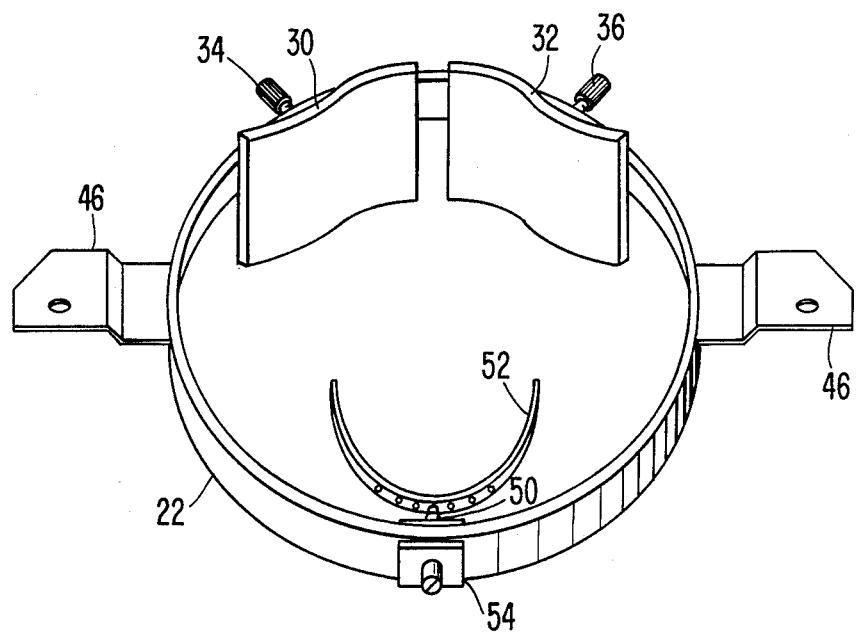
FIG. 5 is a perspective view of an alternative embodiment of the band portion having a maxillary bridge and occipital support pads attached thereto.

FIG. 5 depicts, in perspective view, an alternative embodiment of the maxillary splint means 24 used to engage the maxillary teeth of the wearer. In this embodiment, the band 22 has occipital support pads 30, 32 attached thereto in the same manner as the FIGS. 3, 4 embodiment. The maxillary splint means in FIG. 5 comprises a intermediate bridge support member 50 and a maxillary splint comprising a paraocclusal clutch 52, which is made in a simple unobstructive arch form for the present application. The paraocclusal clutch is preferably made of a metal which is at least partially malleable. The "standard" arch shape may thus be modified as necessary to conform to the outer or gingival surface of the maxillary teeth.

The clutch 52 is then preferably secured to the outer surface of the teeth by reversibly bonding the clutch 52 directly to the enamel of the teeth with an appropriate bonding agent. Reversible bonding (i.e. bonding which may be undone) of such metals to the teeth has begun being used in the field of dentistry, for example, in the so-called "Maryland bridge". Use of the paraocclusal clutch provides the advantage that the upper teeth may be used for many functions such as chewing, and may provide improved hygiene as compared to a mouthpiece-type splint, as well as other advantages.

Once paraocclusal clutch 52 is bonded to the teeth, the band 22 may be connected thereto via bridge 50 which engages an inner portion of clamp 54, which is attached to the ring 22 by clamping force. Occipital support pads 30, 32 may then be adjusted to engage the posterolateral portion of the skull. Once this has been completed, the band may be attached to uprights 18, 20 in the same manner as previously described.

The fixation of the maxillary splint means in the patient's mouth and of the occipital support pads to the posterior aspect of the head, both attached in their final fixed positions to an encircling band, the band further being substantially immobilized by attachment to vest uprights extending upwardly from an upper body support, provides an orthosis which limits motion of the cervical spine as effectively, or nearly as effectively, as the known halo-type orthoses. The aforementioned problems with those known halo-type orthoses are, however, overcome by the present invention.

Preliminary data obtained in connection with the development of the orthosis of the present invention indicate that the orthosis permits only about one to two percent of unrestricted cervical flexion and extension. Further, unrestricted cervical rotation is permitted by the orthosis over only a similar one to two percent range. The range of unrestricted lateral bending allowed by this orthosis is approximately three percent. These motion limits compare very favorably with those attainable in using a conventional halo-type orthosis, and provide substantial improvement over other known devices.

While a preferred embodiment of the invention has been described above, variations and modifications of the device may become readily apparent to those skilled in the art without departing from the spirit and scope of this invention. The proper scope of the invention is therefore to be determined by reference to the appended claims.

We claim:

1. A cervical spine orthosis comprising:
   upper body engaging means for securely engaging an upper body of a wearer of said orthosis;
   maxillary tooth splint means for securely engaging a plurality of superior maxillary teeth of said wearer;
   occipital bone support means for engaging a posterior portion of a head of said wearer at a region where an occipital bone of said wearer's skull is located; and
   means rigidly connecting said maxillary tooth splint means and said occipital support means to said upper body engaging means, wherein relative movement between said maxillary tooth splint means, said occipital support means and said upper body engaging means is substantially prohibited.

2. A cervical spine orthosis as defined in claim 1 wherein said maxillary tooth splint means comprises a mouthpiece formed in a shape to fit snugly on said superior maxillary teeth.

3. A cervical spine orthosis as defined in claim 2 further comprising a band adapted to encircle said head of said wearer, wherein said maxillary tooth splint means is attached to said band at an inner front portion of said band, and said occipital bone support means is attached to said band at an inner rear portion of said band.

4. A cervical spine orthosis as defined in claim 3 wherein said occipital bone support means comprises a first and a second occipital support pad, said first occipital support pad having a contour adapted to engage said posterior portion of said head at a first posterolateral aspect of the occipital bone, and said second occipital support pad having a contour adapted to engage said posterior portion of said head at a second posterolateral aspect of the occipital bone.

5. A cervical spine orthosis as defined in claim 4 wherein said maxillary tooth splint means is disposed at a fixed distance from said band, and wherein said maxillary tooth splint means is attached to said band by an intermediate bridge support, said bridge support being removably fastened to said band and substantially permanently fastened to said maxillary tooth splint means.

6. A cervical spine orthosis as defined in claim 5 wherein said first and second occipital support pads have means for moving said pads to adjust a space between said pads and a perimeter of said band.

7. A cervical spine orthosis as defined in claim 6 wherein said pad moving means comprises a first threaded positioning screw attached to said first occipital support pad and extending through a first tapped bore in said band, and a second threaded positioning screw attached to said second occipital support pad and extending through a second tapped bore in said band.

8. A cervical spine orthosis as defined in claim 3 wherein said upper body engaging means comprises a vest adapted to cover a chest portion of said wearer, a back portion of said wearer and a shoulder portion of said wearer.

9. A cervical spine orthosis as defined in claim 8 wherein said means for rigidly connecting said maxillary tooth splint means and said occipital support means to said vest comprises a first and a second pair of vest upright members, said first vest upright members being attached to a chest portion of said vest, said first pair of vest upright members extending upwardly from said vest, said first pair of vest upright members being secured to portions of said band on opposite sides of a wearer's face, and said second pair of vest upright members being attached to a back portion of said vest, said second pair of vest upright members extending upwardly from said vest, said second pair of vest upright members further having horizontal extension members, said horizontal extension members being secured to portions of said band rearwardly of said first pair of upright members on opposite sides of said wearer's head.

10. A cervical spine orthosis as defined in claim 2 wherein said maxillary tooth splint means is fastened to said plurality of superior maxillary teeth by an acrylic adhesive compound.

11. A cervical spine orthosis as defined in claim 2 wherein said maxillary tooth splint means is fastened to said plurality of superior maxillary teeth by wiring said maxillary tooth splint means to said maxillary teeth.

12. A component for a cervical spine orthosis comprising:
a maxillary tooth splint means for tightly and securely engaging a plurality of superior maxillary teeth of a wearer;
rear support means for engaging a back portion of a head of said wearer; and
means rigidly connecting said splint means and said rear support means to a support member disposed on an upper body of said wearer, wherein relative motion between said splint means, said rear support means and said upper body support member is substantially prohibited.

13. A component for a cervical spine orthosis as defined in claim 12 wherein said means for rigidly connecting said splint means and said rear support means to said support member comprises a band adapted to encircle a head of said wearer at approximately the same level as the mouth of the wearer, said maxillary tooth splint means and said rear support means being attached to said band and extending inwardly therefrom.

14. A component for a cervical spine orthosis as defined in claim 13 wherein said maxillary tooth splint means comprises an acrylic mouthpiece conforming to the shape of said plurality of teeth, and wherein said splint means further has a bridging member attached thereto, said bridging member extending into attachment with an inner surface of a front portion of said band.

15. A component for a cervical spine orthosis as defined in claim 13 wherein said maxillary tooth splint means comprises a paraocclusal clutch adapted to conform to the shape of said plurality of teeth, said paraocclusal clutch being adapted to be reversibly bonded thereto, and wherein said splint means further has a bridging member attached thereto, said bridging member extending into attachment with an inner surface of a front position of said band.

16. A for a cervical spine orthosis as defined in 15, wherein said rear support means comprises of support pads attached to said band and opposite sides of a rear central portion of the band.

17. A for a cervical spine orthosis as defined 16 wherein each of said pair of support pads has means for moving each of said pads into contact with said back portion of said head.

18. A for a cervical spine orthosis as define in 16, wherein each of said moving means comprises a threaded positioning screw attached to an associated support pad, said positioning screws extending through tapped bores in said band.

19. A method for stabilizing a cervical spine of a patient comprising the steps of:
(a) attaching an upper body engaging means to an upper body of said patient;
(b) securing a maxillary tooth splint means to the upper maxillary teeth of said patient;
(c) attaching said maxillary tooth splint means to a band which is adapted to encircle the head of said wearer;
(d) positioning a pair of support pads to brace an occipital bone of said wearer, said support pads being secured to said band at a rear portion thereof; and
(e) connecting, in a rigid manner substantially prohibiting relative movement, said upper body engaging means and said band having said maxillary tooth splint means and said support pads attached thereto.

* * * * *

UNITED STATES PATENT AND TRADEMARK OFFICE
CERTIFICATE OF CORRECTION

PATENT NO. : 4,951,655
DATED : August 28, 1990
INVENTOR(S) : Michael MacMILLAN, ET AL It is certified that error appears in the above-identified patent and that said Letters Patent is hereby corrected as shown below:

Title page:

In the Abstract at line 3: delete "encircul-" and insert -- encircl- --

In the Abstract at line 5: delete "bank" and insert -- band --

In the Abstract at line 10: delete "maxiallary" and insert -- maxillary --

In Claim 16, line 1: after "A" insert -- component --; after "in" insert -- claim --

In Claim 17, line 1: after "A" insert -- component --; after "defined" insert -- in claim --

In Claim 18, line 1: after "A" insert -- component --; delete "define" and insert -- defined --; after "in" insert -- claim --

Signed and Sealed this

Twenty-sixth Day of November, 1991

*Attest:*

HARRY F. MANBECK, JR.

*Attesting Officer*     *Commissioner of Patents and Trademarks*